(12) United States Patent
Schor et al.

(10) Patent No.: US 8,242,108 B2
(45) Date of Patent: Aug. 14, 2012

(54) CELL MIGRATION MODULATING COMPOUNDS

(75) Inventors: Ana Maria Schor, Dundee (GB); Seth Lawrence Schor, Dundee (GB); Rodolfo Marquez, Mauchline (GB); David George Norman, Nr Doune (GB)

(73) Assignee: University of Dundee (GB)

( * ) Notice: Subject to any disclaimer, the term of this patent is extended or adjusted under 35 U.S.C. 154(b) by 315 days.

(21) Appl. No.: 12/064,535

(22) PCT Filed: Aug. 23, 2006

(86) PCT No.: PCT/GB2006/003140
§ 371 (c)(1),
(2), (4) Date: Jun. 26, 2008

(87) PCT Pub. No.: WO2007/023273
PCT Pub. Date: Mar. 1, 2007

(65) Prior Publication Data
US 2009/0221561 A1    Sep. 3, 2009

(30) Foreign Application Priority Data
Aug. 24, 2005    (GB) .................................. 0517292.9

(51) Int. Cl.
*A01N 43/62* (2006.01)
*A61K 31/55* (2006.01)
*C07D 243/12* (2006.01)
(52) U.S. Cl. ........................................ 514/221; 540/504
(58) Field of Classification Search .................. 514/221; 540/504
See application file for complete search history.

(56) References Cited

U.S. PATENT DOCUMENTS
6,458,784 B1 * 10/2002 Cousins et al. ............... 514/221
2004/0014964 A1    1/2004 Cheesman et al.

FOREIGN PATENT DOCUMENTS
WO    WO 9100856    *    1/1991
WO    WO 9414776    *    7/1994
WO    WO 98/04247 A1    2/1998
WO    WO 0063186 A1 *    10/2000

OTHER PUBLICATIONS

Hudkins et. al., Bioorganic and Medicinal Chemistry Letters, 1998, Pergamon, vol. 8, pp. 1873-1876.*
Olesen, Current Opinion in Drug Discovery & Development, 2001, Thomson Reuters, vol. 4, No. 4, pp. 471-478.*
Stork et. al., JACS, 1951, American Chemical Society, vol. 73, No. 10, pp. 4743-4748.*
Tamoto et. al., Chemical and Pharmaceutical Bulletin, 1984, Nihon Yakugakkai, vol. 32, No. 11, pp. 4340-4349.*
Terashima et. al., Tetrahedron Letters, 1983, Pergamon, vol. 24, No. 25, pp. 2589-2592.*
Lin et. al., Bioorganic & Medicinal Chemistry Letters, 1999, Pergamon, vol. 9, pp. 2747-2752.*
Zhou et. al., Bioorganic & Medicinal Chemistry Letters, 2003, Pergamon, vol. 13, pp. 3565-3569.*
Notification of Transmittal of the International Search Report and the Written Opinion of the International Searching Authority, or the Declaration corresponding to International Application No. PCT/GB2006/003140 mailed Nov. 13, 2006.

* cited by examiner

*Primary Examiner* — Sreeni Padmanabhan
*Assistant Examiner* — Sarah Pihonak
(74) *Attorney, Agent, or Firm* — Myers Bigel Sibley & Sajovec, P.A.

(57) ABSTRACT

The described invention relates to compounds which modulate cell migration, and find use in, for example, wound healing, cancer progression and angiogenesis.

7 Claims, 2 Drawing Sheets

```
fnI-1  PGCYDNG--KHYQINQQWERTY-LG-NVLVCTCYGGSRGF-NCESKPEAE
fnI-2  ETCFDKYTGNTYRVGDTYERPKDS--MIWDCTCIGAGRGRISCTIA
fnI-3  NRCHEG--GQSYKIGDTWRRPHETGGYMLECVCLGNGKGEWTCKPIA
fnI-4  EKCFDHAAGTSYVVGETWEKPY-QGWMMVDCTCLGEGSGRITCTSR
fnI-5  NRCNDQDTRTSYRIGDTWSKKDNRGN-LLQCICTGNGRGEWKCERHTSVQ
fnI-6  GHCVTDS-GVVYSVGMQWLKTQ--GNKQMLCTCLGNG---VSCQE
fnI-7  EICTTNE-GVMYRIGDQWDKQHDMG-HMMRCTCVGNGRGEWTCYAYSQLR
fnI-8  DQCIVD--DITYNVNDTFHKRHEEG-HMLNCTCFGQGRGRWKCDPV
fnI-9  DQCQDSETGTFYQIGDSWEKYVH-GVR-YQCYCYGRGIGEWHCQP
```

Figure 1

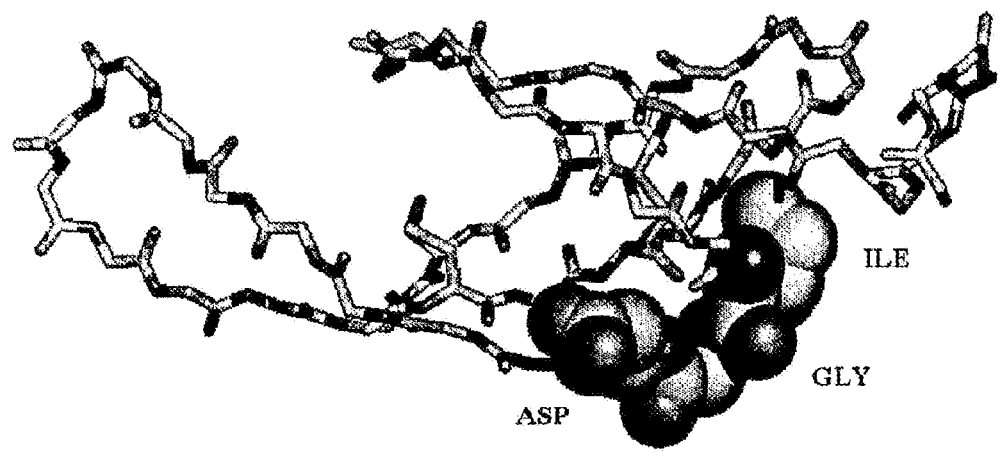

Figure 2

CELL MIGRATION MODULATING COMPOUNDS

RELATED APPLICATIONS

The present application is a 35 U.S.C. §371 national phase application of PCT International Application No. PCT/GB2006/003140, having an international filing date of Aug. 23, 2006 and claiming priority to Great Britain Application No. 0517292.9, filed Aug. 24, 2005, the disclosures of which are incorporated herein by reference in their entireties. The above PCT International Application was published in the English language and has International Publication No. WO 2007/023273 A1.

STATEMENT REGARDING ELECTRONIC FILING OF A SEQUENCE LISTING

A Sequence Listing in ASCII text format, submitted under 37 C.F.R. §1.821, entitled 9013-85_ST25.txt, 4,436 bytes in size, generated on Jun. 21, 2012 and filed via EFS-Web, is provided in lieu of a paper copy. This Sequence Listing is hereby incorporated herein by reference into the specification for its disclosures.

INTRODUCTION

The present invention relates to compounds which modulate cell migration, and find use in, for example, wound healing, cancer progression and angiogenesis.

BACKGROUND

Migration Stimulating Factor (MSF) is a stress-response molecule expressed by epithelial and stromal cells in fetal skin and common human tumours. MSF is not normally present in healthy adult skin, but is transiently re-expressed during wound healing. Human recombinant MSF displays a number of potent bioactivities relevant to wound healing and cancer progression, including the stimulation of cell migration (target: carcinoma cells, keratinocytes, dermal fibroblasts, endothelial cells), stimulation of hyaluronan synthesis by fibroblasts, and angiogenesis in vivo and in vitro (S. L. Schor, I. R. Ellis, S. J. Jones, R. Baillie, K. Seneviratne, J. Clausen, K. Montegi, B. Vojtesek, K. Kankova, E. Furrie, M. J. Sales, A. M. Schor, R. A. Kay. *Cancer Res.* 2003, 63, 8827; and S. L. Schor, A. M. Schor, R. P. Keatch, J. J. F. Belch. *The Wound Healing Manual* McGraw Hill, New York, 2005, pp. 109-121.).

MSF is a truncated isoform of fibronectin produced from the primary fibronectin gene transcript by a bypass of normal alternative splicing involving read-through of the intron separating exons III-1a and -1b. Intron retention results in the inclusion of a unique 30 bp coding sequence. MSF protein is consequently identical to the 70 kDa N-terminus of fibronectin, including nine type I and two type II modules, and terminates with the sequence coded by module III-1a and a unique decamer not present in any previously described "full-length" fibronectin isoform.

The IGD (isoleucine, glycine, aspartate) tripeptide motif, a highly conserved feature of the fibronectin type I module, is present within the third, fifth, seventh and ninth constituent type I modules of MSF (FIG. 1) (R. Hynes, 'Fibronectins', Springer-Verlag, New York, 1990). Interestingly, synthetic trimer and tetramer peptides containing the IGD motif exhibit the same range of biological activities as those displayed by MSF (S. L. Schor, I. Ellis, J. Banyard, and A. M. Schor, *Journal of Cell Science*, 1999, 112, 3879). Furthermore, in vitro mutagenesis and analysis of IGD-recombinant constructs has demonstrated that the motogenic activity of MSF on target fibroblasts is mediated by the IGD sequences.

Studies have implicated the related RGD amino acid motif (located in the tenth type III repeat module) in mediating the cell migrating stimulating effects of both native fibronectin and its cell-binding domain. Significantly, small RGD-containing synthetic peptides did not stimulate cell migration; indeed, these peptides inhibited the adhesive and migration stimulatory activity of larger protein domains contining the RGD motif by competition for receptor ligation.

International patent application published under number WO 99/02674, relates to peptides containing the IGD motif and their use as cell migration modulators.

There is a need to provide molecules which express MSF/IGD bioactivities and show improved stability compared to the IGD tripeptide. Such molecules may be useful as therapeutic agents for the management of patients with impaired wound healing and other pathologies requiring the stimulation of cell migration and angiogenesis.

It is an object of the present invention to provide IGD mimetic molecules having MSF and/or IGD bioactivity, such as stimulatory and/or inhibitory activity.

SUMMARY OF THE INVENTION

According to a first aspect of the present invention there is provided a compound according to formula (I):

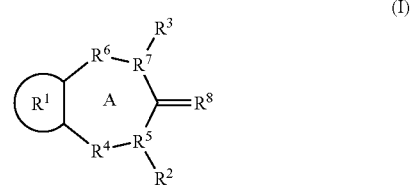

wherein, $R^1$ is a substituted or unsubstituted monocyclic or polycyclic aryl or heteroaryl moiety;

$R^2$ is a carboxylic acid or carboxylate ester thereof, including isoteres thereof, bonded to $R^5$ either directly or via a group which is independently selected from —O—, —S—, —$NR^9$— or —$(CCR^{10}R^{11})_n$—;

$R^3$ is selected from the group consisting of H, branched or unbranched substituted or unsubstituted linear or cyclic alkyl, branched or unbranched substituted or unsubstituted linear or cyclic alkenyl, branched or unbranched substituted or unsubstituted linear or cyclic alkynyl, or substituted or unsubstituted monocyclic or polycyclic aryl or heteroaryl. $R^3$ may be bonded to $R^7$ either directly or via a group which is selected from —O—, —S—, —$NR^9$— or —$(CR^{10}R^{11})_n$—;

$R^4$ and $R^6$ may be individually absent or present, and when present are independently selected from the group consisting of —O—, —S—, —$NR^9$— or —$(CR^{10}R^{11})_m$—;

$R^5$ is selected from the group consisting of —N—, —$(CR^{10})_m$— or —X—;

$R^7$ may be absent or present, and when present, is selected from the group consisting of —N—, —$(CR^{10})_m$ or —X—;

$R^8$ is selected from the group consisting of O, S, Se, $NR^9$ or $CR^{10}R^{11}$;

$R^9$ at each occurrence is independently selected from the group consisting of H, branched or unbranched substituted or unsubstituted linear or cyclic alkyl, branched or unbranched substituted or unsubstituted linear or cyclic alkenyl, branched or unbranched substituted or unsubstituted linear or cyclic alkynyl, substituted or unsubstituted monocyclic or polycyclic aryl or heteroaryl;

$R^{10}$ and $R^{11}$ are independently, at each occurrence, selected from the group consisting of H, branched or unbranched substituted or unsubstituted linear or cyclic alkyl, branched or unbranched substituted or unsubstituted linear or cyclic alkenyl, branched or unbranched substituted or unsubstituted linear or cyclic alkynyl, or substituted or unsubstituted monocyclic or polycyclic aryl or heteroaryl, carboxy, alkyloxycarbonyl hydroxyl, amino, nitro, alkyloxy, alkylthio, formyl, cyano, carbamoyl, halo (e.g. fluoro, chloro, bromo or iodo), a ketone, —S(O)NR$^{12}$R$^{13}$ or —S(O)R$^{14}$, wherein $R^{12}$, $R^{13}$ and $R^{14}$ each independently have the same definition as that given for $R^3$ herein, n is from 1 to 25;

m is from 1 to 4; and

X is a heteroatom;

provided that the ring A is not less than a 6 membered ring; or a physiologically acceptable salt, ester or other physiologically functional derivative thereof.

In formula (I), for example, the $R^1$ aryl moiety may be a 5 or 6-membered monocyclic aryl or heteroaryl ring structure or other polycyclic aryl or heteroaryl moiety.

Phenyl is an example of a 6-membered aryl group.

Typically, the heteroatom in the heteroaryl structure is selected from oxygen or nitrogen.

Furyl and pyrrolyl are examples of 5-membered heteroaryl groups containing an oxygen and a nitrogen heteroatom respectively.

Pyridinyl and pyrimidinyl are examples of 6-membered heteroaryl groups containing one nitrogen and two nitrogen atoms respectively.

Naphthyl is an example of a polycyclic aryl group which has a 10 carbon atom framework formed as two fused 6-membered rings.

As indicated, the $R^1$ group may be substituted at one or more positions, and suitable substituents may be independently selected, at each substituent position, from those substituents which define $R^{10}$ and $R^{11}$.

The subsituents may be bonded to $R^1$ directly or via a group which is independently selected from —O—, —S—, —N— or —(CR$^{10}$R$^{11}$)$_n$— wherein, n, $R^{10}$ and $R^{11}$ have the same definitions as defined hereinbefore.

As indicated, $R^2$ includes carboxylate ester isosteres, of which an amide is an example. An isostere may be defined as a compound which exhibits similar properties with another different compound as a result of having the same number of total or valence electrons in the same arrangement and which consists of different atoms, and not necessarily the same number of atoms.

The nitrogen atom of the amide may be unsubstituted or substituted, for example, typical substituents may be chosen from those which define $R^9$.

As an option, n may instead, take a value of from 1 to 10 or alternatively from 1 to 4.

Suitable heteroatoms from which X may be chosen include any of O, S, P, Se, Si or As.

By ring A being not less than a 6 membered ring we mean that, for example, if $R^4$ is absent, then both $R^6$ and $R^7$ must be present. Alternatively, if $R^4$ and $R^6$ are absent and $R^7$ is a —(CR$^{10}$)$_m$— group, then m should at least take a value of 2, which ensures that the ring A is a 6 membered ring.

Preferably, ring A is a 7 membered ring.

A preferred compound of formula (I) has the following formula (II):

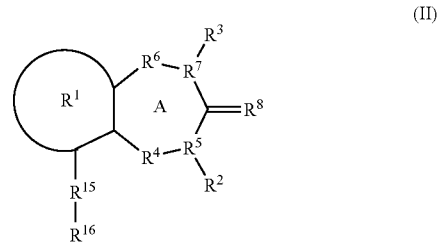

(II)

wherein, $R^1$, $R^2$, $R^3$, $R^4$, $R^5$, $R^6$, $R^7$ and $R^8$ are as defined herein before;

$R^{15}$ is selected from —O—, —S— or —NR$^9$—, wherein $R^9$ is defined as herein before;

$R^{16}$ independently is a group selected from those which define $R^9$; or a physiologically acceptable salt, ester or other physiologically functional derivative thereof.

Preferably, ring A in formula (II) is a 7 membered ring.

In the formulae (I) or (II), preferably, and independently, that is, alone or in combination, $R^1$ is a phenyl group;

$R^2$ is a carboxylic acid alkyl ester bonded to $R^5$ either directly or via a group which is independently selected from —O—, —S—, —NR$^9$— or —(CH$_2$)—;

$R^3$ and $R^{16}$ are independently selected from a branched or unbranched substituted or unsubstituted linear or cyclic alkyl group, or a substituted or unsubstituted monocyclic or polycyclic aryl or heteroaryl group;

$R^4$ is —O— or —NR$^9$—, wherein $R^9$ is H or branched or unbranched substituted or unsubstituted linear or cyclic alkyl group, or a substituted or unsubstituted monocyclic or polycyclic aryl or heteroaryl group;

$R^5$ is —(CR$^{10}$)$_m$—, wherein $R^{10}$ is as defined hereinbefore;

$R^6$ is CH$_2$;

$R^7$ is as defined hereinbefore;

$R^8$ is O or S; and $R^{15}$ is as defined hereinbefore.

Preferably, $R^2$ is bonded to $R^5$ via —(CH$_2$)—, $R^4$ and $R^7$ are each —NR$^9$—, wherein $R^9$ is H or a branched or unbranched substituted or unsubstituted linear or cyclic alkyl group, and $R^{15}$ is —O—.

Thus, preferred compounds of the present invention are described by formula (III):

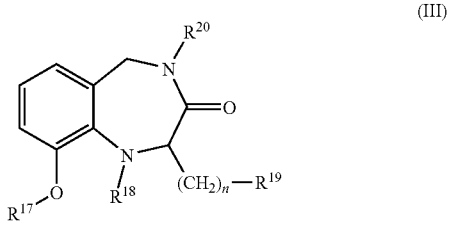

(III)

wherein, $R^{17}$ and $R^{20}$ are independently selected from H, a branched or unbranched substituted or unsubstituted linear or cyclic alkyl group, or a substituted or unsubstituted monocyclic or polycyclic aryl or heteroaryl group;

$R^{18}$ is H or a branched or unbranched substituted or unsubstituted linear or cyclic alkyl group;

$R^{19}$ is $CO_2R^{21}$;

$R^{21}$ is a branched or unbranched substituted or unsubstituted linear or cyclic alkyl group; and n is as defined hereinbefore; or a physiologically acceptable salt, ester or other physiologically functional derivative thereof.

Without wishing to be bound by theory, the usefulness of the molecules described herein is believed to be related to the ability of those molecules to mimic the IGD tripeptide motif which is found in Migration Stimulating Factor (MSF) which is referred to herein. The letters I, G and D refer to the standard peptide nomenclature and hence refer to isoleucine, glycine and aspartate respectively, and IGD therefore represents the tripeptide Ile-Gly-Asp.

Careful examination of the NMR structural information available for the fnI-5 and fnI-7 modules (which are shown in FIG. 1) revealed that the desired IGD motif is present as a tightly structured peptide turn (FIG. 2). It is believed that it is this highly conserved structure which is then recognised by the relevant cell receptors (M. Baron, D. Norman, A. Willis, and I. D. Campbell, *Nature*, 1990, 345, 642; M. J. Williams, I. Phan, T. S. Harvey, A. Rostagno, L. I. Gold, and I. D. Campbell, *Journal of Molecular Biology*, 1994, 235, 1302; and A. D. Becke, *Journal of Chemical Physics*, 1993, 98, 1372).

The observation that the IGD containing loops in fnI-5 and fnI-7 are tightly defined (unlike most of the known RGD containing loops which are largely unstructured and flexible), provides an appropriate basis to develop small molecule IGD peptidomimetics which display similar geometrical and stereo-electronic arrangements to those observed in the fnI structure and which may therefore be recognised by the MSF (IGD) receptors. Successful receptor recognition may translate into a similar dose-response curve to that of an IGD peptide and, by extension, to that of intact MSF.

MSF displays bioactivies relating to stimulation of cell migration, stimulation of hyaluronan synthesis by fibroblasts, angiogenesis (new blood vessel formation) and tumor growth, and therefore the compounds of the present invention are useful in medicine.

Accordingly, according to a second aspect of the present invention, there is provided a compound according to the first aspect e.g. according to formulae (I), (II) or (III) as described hereinbefore, for use in medicine.

In particular, without wishing to be bound by any particular theory, agonists of MSF are expected to help treat and/or promote the healing process of slow healing wounds. An antagonist of MSF may be useful to prevent or reduce the growth of tumors because many tumors use MSF to promote vascularisation.

Accordingly, the present invention therefore includes compounds as hereinbefore defined as agonists or antagonists of MSF.

In adult mammals MSF is barely detectable outside pathological situations and therefore an antagonist of MSF may be able to disrupt tumor vascularisation, growth and metastasis selectively, that is, without affecting the normal growth mechanisms of the mammal.

According to a third aspect of the present invention, there is provided a pharmaceutical composition comprising a compound according to the first aspect e.g. according to formulae (I), (II) or (III) as described hereinbefore, together with a pharmaceutically acceptable carrier therefor.

Impaired cell migration is often a feature of clinical conditions in which wound healing is not optimal and the stimulation of cell migration under these conditions may prove beneficial. Conversely, elevated or inappropriate cell migration is a feature of several pathological conditions, including tumor invasion, pathological angiogenesis, inflammation and fibrosis. Inhibitors of IGD bioactivity may prove useful in the treatment of these conditions.

According to a fourth aspect of the present invention, there is provided use of a compound according to the first aspect e.g. according to formulae (I), (II) or (III) as described hereinbefore, for the preparation of a medicament for wound healing or for use in other pathologies requiring modulation of cell migration.

For example the compounds of the present invention may be used to promote or inhibit the IGD bioactivity appropriate to the situation requiring attention.

As such, the compounds may be used for stimulating cell migration and/or angiogenesis, especially in wound healing or periodontal tissue regeneration or inhibiting cell migration in, for example, inhibition of tumour invasion and metastatis, inhibiting pathological angiogenesis, inflammation and fibrosis.

Promotion of wound healing is particularly beneficial in the treatment of ulcers which can be chronic and resistant to treatment in, for example, diabetic and elderly patients, e.g. leg ulcers and bed sores.

The compounds of the present invention may also be used in the treatment of corneal wounds.

According to a fifth aspect of the present invention there is provided a method of modulating cell migration, the method comprising applying an effective amount of a compound according to the first aspect e.g. according to formulae (I), (II) or (III) as described hereinbefore to a site where modulation of cell migration is desired.

Cell migration may be modulated according to the method of the fifth aspect of the invention ex vivo or in vitro, for example in cell culture; or cell migration may be modulated in vivo.

Migration may be modulated in a cell selected from carcinoma cells, keratinocytes, dermal fibroblasts or endothelial cells.

It is preferred that fibroblast cell migration is modulated.

In the compound formulae described herein, an alkyl group may be independently a $C_1$-$C_{22}$ alkyl, preferably a $C_1$-$C_{10}$ alkyl, preferably $C_1$-$C_4$ alkyl, for example, methyl, ethyl, propyl, butyl.

An alkenyl group may be independently a $C_2$-$C_{22}$ alkenyl, preferably a $C_2$-$C_{10}$ alkenyl, preferably $C_2$-$C_4$ alkenyl.

An alkynyl group may be independently a $C_2$-$C_{22}$ alkynyl, preferably a $C_2$-$C_{10}$ alkynyl, preferably $C_2$-$C_4$ alkynyl.

The alkyl, alkenyl or alkynyl groups may be branched or unbranched, substituted or unsubstituted. For example typical branched alkyl groups include iso-propyl, iso-butyl, sec-butyl, tert-butyl, 3-methylbutyl, 3,3-dimethylbutyl and variations, including isomers thereof.

As described herein, the alkyl, alkenyl or alkynyl groups may be substituted, and the substituents may be any chemical moiety such as a hydroxyl, substituted or unsubstituted amine, substituted or unsubstituted amide, halide (such as fluoro, chloro, bromo, iodo), alkoxy, thio, nitro, carboxy, an ester, cyano, or aryl (such as phenyl, naphyl and pyridyl).

The geometry of the double bonds in the alkenyl groups may be in the cis- or trans-geometry.

Examples of physiologically acceptable salts of the compounds according to the invention include acid addition salts formed with organic carboxylic acids such as acetic, lactic, tartaric, maleic, citric, pyruvic, oxalic, fumaric, oxaloacetic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids.

Physiologically functional derivatives of compounds of the present invention are derivatives which can be converted in the body into the parent compound. Such physiologically functional derivatives may also be referred to as "pro-drugs" or "bioprecursors". Physiologically functional derivatives of compounds of the present invention include in vivo hydrolysable esters.

It will be appreciated that the compounds of the present invention may exist in various stereoisomeric forms and the compounds of the present invention as hereinbefore defined include all stereoisomeric forms and mixtures thereof, including enantiomers and racemic mixtures. The present invention includes within its scope the use of any such stereoisomeric form or mixture of stereoisomers, including the individual enantiomers of the compounds of formulae (I), (II) or (III) as well as wholly or partially racemic mixtures of such enantiomers.

A preferred configuration for the compounds according to formula (III) is that represented by formula (IIIA):

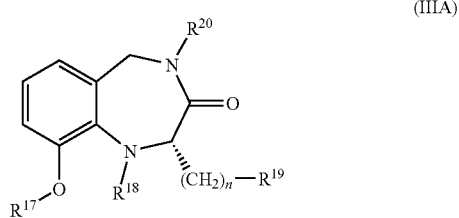

(IIIA)

wherein $R^{17}$, $R^{18}$, $R^{19}$ and $R^{20}$ are as defined hereinbefore.

A preferred compound of the present invention has the formula (IV):

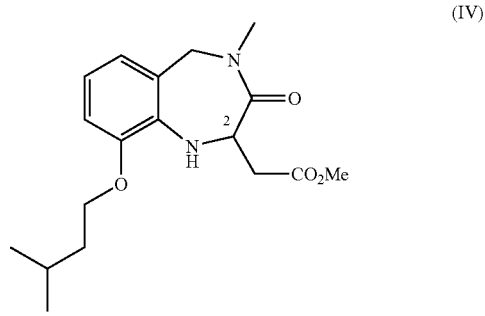

(IV)

This compound according to formula (IV) is believed to be novel and as such forms a further feature of this invention.

Preferably, the stereochemistry about the carbon atom shown at position 2 is defined by an S-configuration.

The compounds of the present invention may be prepared using reagents and techniques readily available in the art and as described hereinafter. Novel intermediate compounds in the synthetic route for preparation of the compounds of the present invention may be important molecules for general application for the preparation of the molecules of the present invention. Accordingly, the present invention extends to include those novel intermediate compounds.

The present invention further provides a treatment or prophylaxis of a disease, pathology or condition recited herein comprising administering a compound recited herein to a patient in need thereof.

The patient is typically an animal, e.g a mammal, especially a human.

For use according to the present invention, the compounds or physiologically acceptable salt, ester or other physiologically functional derivative thereof described herein may be presented as a pharmaceutical formulation, comprising the compound or physiologically acceptable salt, ester or other physiologically functional derivative thereof, together with one or more pharmaceutically acceptable carriers therefore and optionally other therapeutic and/or prophylactic ingredients. The carrier(s) must be acceptable in the sense of being compatible with the other ingredients of the formulation and not deleterious to the recipient thereof.

Pharmaceutical formulations include those suitable for oral, topical (including dermal, buccal and sublingual), rectal or parenteral (including subcutaneous, intradermal, intramuscular and intravenous), nasal and pulmonary administration e.g., by inhalation. The formulation may, where appropriate, be conveniently presented in discrete dosage units and may be prepared by any of the methods well known in the art of pharmacy. All methods include the step of bringing into association an active compound with liquid carriers or finely divided solid carriers or both and then, if necessary, shaping the product into the desired formulation.

Pharmaceutical formulations suitable for oral administration wherein the carrier is a solid are most preferably presented as unit dose formulations such as boluses, capsules or tablets each containing a predetermined amount of active compound. A tablet may be made by compression or moulding, optionally with one or more accessory ingredients. Compressed tablets may be prepared by compressing in a suitable machine an active compound in a free-flowing form such as a powder or granules optionally mixed with a binder, lubricant, inert diluent, lubricating agent, surface-active agent or dispersing agent. Moulded tablets may be made by moulding an active compound with an inert liquid diluent. Tablets may be optionally coated and, if uncoated, may optionally be scored. Capsules may be prepared by filling an active compound, either alone or in admixture with one or more accessory ingredients, into the capsule shells and then sealing them in the usual manner. Cachets are analogous to capsules wherein an active compound together with any accessory ingredient(s) is sealed in a rice paper envelope. An active compound may also be formulated as dispersable granules, which may for example be suspended in water before administration, or sprinkled on food. The granules may be packaged, e.g., in a sachet. Formulations suitable for oral administration wherein the carrier is a liquid may be presented as a solution or a suspension in an aqueous or non-aqueous liquid, or as an oil-in-water liquid emulsion.

Formulations for oral administration include controlled release dosage forms, e.g., tablets wherein an active compound is formulated in an appropriate release-controlling matrix, or is coated with a suitable release-controlling film. Such formulations may be particularly convenient for prophylactic use.

Pharmaceutical formulations suitable for rectal administration wherein the carrier is a solid are most preferably presented as unit dose suppositories. Suitable carriers include cocoa butter and other materials commonly used in the art. The suppositories may be conveniently formed by admixture of an active compound with the softened or melted carrier(s) followed by chilling and shaping in moulds.

Pharmaceutical formulations suitable for parenteral administration include sterile solutions or suspensions of an active compound in aqueous or oleaginous vehicles.

Injectable preparations may be adapted for bolus injection or continuous infusion. Such preparations are conveniently presented in unit dose or multi-dose containers which are sealed after introduction of the formulation until required for use. Alternatively, an active compound may be in powder form which is constituted with a suitable vehicle, such as sterile, pyrogen-free water, before use.

An active compound may also be formulated as long-acting depot preparations, which may be administered by intramuscular injection or by implantation, e.g., subcutaneously or intramuscularly. Depot preparations may include, for example, suitable polymeric or hydrophobic materials, or ion-exchange resins. Such long-acting formulations are particularly convenient for prophylactic use.

Formulations suitable for pulmonary administration via the buccal cavity are presented such that particles containing an active compound and desirably having a diameter in the range of 0.5 to 7 microns are delivered in the bronchial tree of the recipient.

As one possibility such formulations are in the form of finely comminuted powders which may conveniently be presented either in a pierceable capsule, suitably of, for example, gelatin, for use in an inhalation device, or alternatively as a self-propelling formulation comprising an active compound, a suitable liquid or gaseous propellant and optionally other ingredients such as a surfactant and/or a solid diluent. Suitable liquid propellants include propane and the chlorofluorocarbons, and suitable gaseous propellants include carbon dioxide. Self-propelling formulations may also be employed wherein an active compound is dispensed in the form of droplets of solution or suspension.

Such self-propelling formulations are analogous to those known in the art and may be prepared by established procedures. Suitably they are presented in a container provided with either a manually-operable or automatically functioning valve having the desired spray characteristics; advantageously the valve is of a metered type delivering a fixed volume, for example, 25 to 100 microliters, upon each operation thereof.

As a further possibility an active compound may be in the form of a solution or suspension for use in an atomizer or nebuliser whereby an accelerated airstream or ultrasonic agitation is employed to produce a fine droplet mist for inhalation.

Formulations suitable for nasal administration include preparations generally similar to those described above for pulmonary administration. When dispensed such formulations should desirably have a particle diameter in the range 10 to 200 microns to enable retention in the nasal cavity; this may be achieved by, as appropriate, use of a powder of a suitable particle size or choice of an appropriate valve. Other suitable formulations include coarse powders having a particle diameter in the range 20 to 500 microns, for administration by rapid inhalation through the nasal passage from a container held close up to the nose, and nasal drops comprising 0.2 to 5% w/v of an active compound in aqueous or oily solution or suspension.

It should be understood that in addition to the aforementioned carrier ingredients the pharmaceutical formulations described above may include, an appropriate one or more additional carrier ingredients such as diluents, buffers, flavouring agents, binders, surface active agents, thickeners, lubricants, preservatives (including anti-oxidants) and the like, and substances included for the purpose of rendering the formulation isotonic with the blood of the intended recipient.

Pharmaceutically acceptable carriers are well known to those skilled in the art and include, but are not limited to, 0.1 M and preferably 0.05 M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Preservatives and other additives may also be present, such as, for example, antimicrobials, antioxidants, chelating agents, inert gases and the like.

Formulations suitable for topical formulation may be provided for example as gels, creams or ointments. Such preparations may be applied e.g. to a wound or ulcer either directly spread upon the surface of the wound or ulcer or carried on a suitable support such as a bandage, gauze, mesh or the like which may be applied to and over the area to be treated.

Liquid or powder formulations may also be provided which can be sprayed or sprinkled directly onto the site to be treated, e.g. a wound or ulcer. Alternatively, a carrier such as a bandage, gauze, mesh or the like can be sprayed or sprinkle with the formulation and then applied to the site to be treated.

Therapeutic formulations for veterinary use may conveniently be in either powder or liquid concentrate form. In accordance with standard veterinary formulation practice, conventional water soluble excipients, such as lactose or sucrose, may be incorporated in the powders to improve their physical properties. Thus particularly suitable powders of this invention comprise 50 to 100% w/w and preferably 60 to 80% w/w of the active ingredient(s) and 0 to 50% w/w and preferably 20 to 40% w/w of conventional veterinary excipients. These powders may either be added to animal feedstuffs, for example by way of an intermediate premix, or diluted in animal drinking water.

Liquid concentrates of this invention suitably contain the compound or a derivative or salt thereof and may optionally include a veterinarily acceptable water-miscible solvent, for example polyethylene glycol, propylene glycol, glycerol, glycerol formal or such a solvent mixed with up to 30% v/v of ethanol. The liquid concentrates may be administered to the drinking water of animals.

The present invention will now be described with reference to the following non-limiting examples.

BRIEF DESCRIPTION OF DRAWINGS

The present invention will now be described with reference to the following drawings in which:

FIG. 1 is a schematic representation of the first to ninth constituent modules (SEQ ID NOS:1-9, respectively) of the fibronectin type I module (fnI). The primary sequence of the fibronectin/MSF type I modules is shown, with the IGD sequences shown in bold and dark-grey highlight, and the conserved cysteine positions are indicated by light-grey highlight;

FIG. 2 is a three dimensional representation of the structure of fnI-7 backbone with space filling representation of the IGD motif;

DETAILED DESCRIPTION

Compound Synthesis

Figure 3:
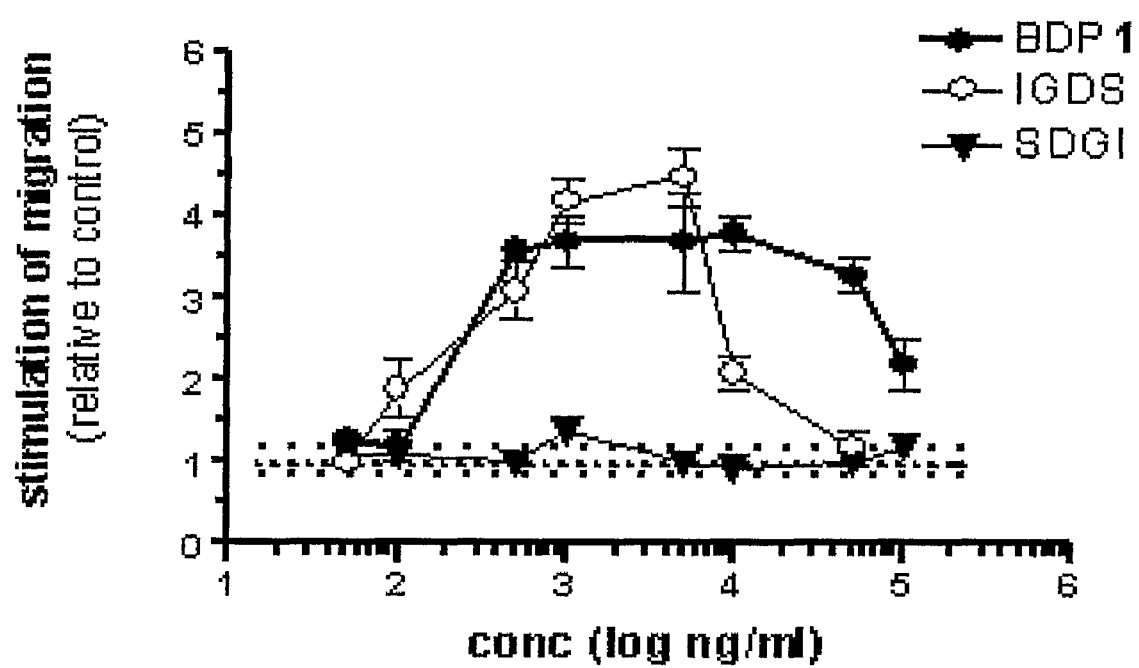
FIG. 3 is a graph plot showing the effects of compound (IV) (BDP 1) and the synthetic peptides IGDS and SDGI on fibroblast migration.

Compound (IV) as described herein was provided according to the following method, with reference to Schemes 1 and 2.

Referring to Scheme 1, commercially available nitrocresol 3, was cleanly alkylated and then brominated under radical conditions to generate the benzylic bromide 4 together with a small amount of the undesired dibromide 5 as an inseparable mixture of compounds (D. D. Tanner, C. P. Meintzer, E. C. Tsai, and H. Oumarmahamat, *Journal of the American Chemical Society*, 1990, 112, 7369; M. E. Krolski, A. F. Renaldo, D. E. Rudisill, and J. K. Stille, *Journal of Organic Chemistry*, 1988, 53, 1170).

An efficient SN2 nucleophilic substitution of methylamine to the benzylic bromides 4 and 5 then proceeded to cleanly afford the desired benzyl amines 6 and 7 respectively (B. C. Soderberg, S. R. Rector, and S, N, O'Neil, *Tetrahedron Letters*, 1999, 40, 3657). BOC protection of the newly introduced benzylic amine then generated the nitrobenzene units 8 and 9, which under palladium hydrogenation conditions reduced both the nitro and the tertiary bromide functionalities to produce the free amine unit 10 as a single compound (W. H. Miller, K. A. Newlander, D. S. Eggleston, and R. C. Haltiwanger, *Tetrahedron Letters*, 1995, 36, 373).

Referring to Scheme 2, condensation of aniline 10 with dimethyl acetylenedicarboxylate proceeded cleanly to produce the expected dimethyl diester 11 (W. E. Bondinell, W. H. Miller, F. E. Ali, A. C. Allen, C. W. DeBrosse, D. S. Eggleston, K. F. Erhard, R. C. Hatiwanger, W. F. Huffman, S.-M. Hwang, D. R. Jakas, P. F. Koster, T. W. Ku, C. P. Lee, A. J. Nichols, S. T. Ross, J. M. Samanen, R. E. Valocik, J. A. Vasko-Moser, J. W. Venlavsky, A. S. Wong, C.-K. Yuan., *Bioorg. Med. Chem.*, 1994, 2, 897). Palladium mediated hydrogenation of the alkene double bond reduction then afforded the desired diester 12 as a racemic mixture.

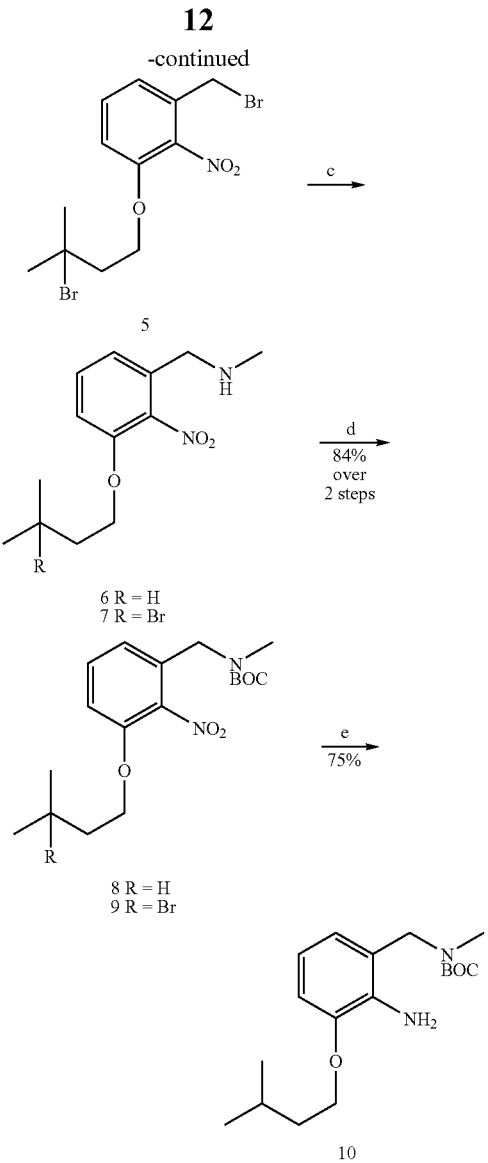

Reagents and Conditions: a) Isobutyl bromide, K₂CO₃, DMF, RT, 24 h; b) NBS, AIBN, CCl₄, reflux, 12 h; c) CH₃NH₂ (40% in H₂O), THF, RT, 12 h; d) BOC₂O, TEA, DMAP, CH₂Cl₂, 0° C. - RT, 12 h; e) Pd/C (10%), H₂, CH₃OH, RT, 3 h.

Finally, efficient removal of the BOC protecting group afforded the free benzylic methyl amine 13 in excellent yield, which was then selectively cyclised with the adjacent methyl ester to generate compound (IV).

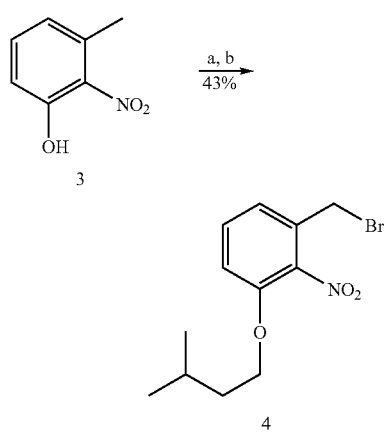

Scheme 1

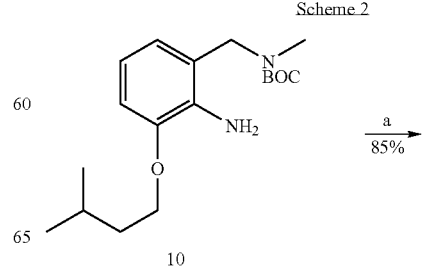

Scheme 2

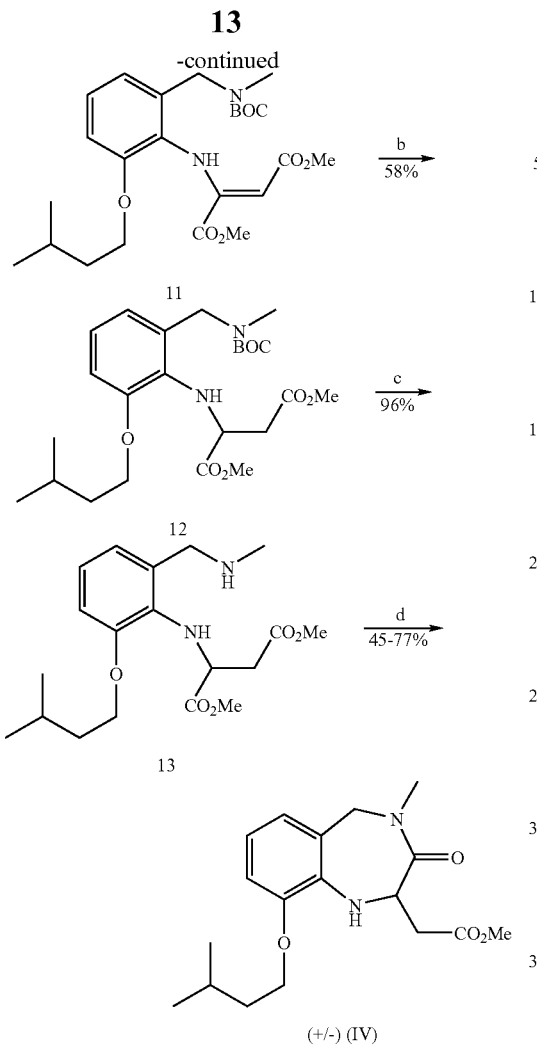

Reagents and Conditions: a) MeO₂CCCCO₂Me, CH₃OH, reflux, 1 h; b) Pd/C (10%), H₂, CH₃OH, RT, 30 min; c) TFA, CH₂Cl₂, 0° C., 1 h; d) NaOCH₃ (25% in CH₃OH), RT, 1 h.

NMR analysis of compound (IV) provided the following data:

$^1$H NMR (300 MHz, CDCl$_3$) $\delta_H$ 6.64 (1H, dd, J=7.0, 2.4 Hz), 6.54-6.46 (2H, m), 5.41 (1H, d, J=16.3 Hz), 5.03-4.97 (1H, m), 4.34 (1H, d, J=4.2 Hz), 3.94-3.86 (2H, m), 3.66 (3H, s), 3.64 (1H, d, J=16.2 Hz), 2.99 (3H, s), 2.98 (1H, dd, J=15.8, 7.4 Hz), 2.61 (1H, dd, J=15.8, 6.3 Hz), 1.76-1.69 (1H, m), 1.61 (2H, q, J=6.6 Hz), 0.89.

Biological Assesment

The potency and efficacy of the IGD mimetic (IV) was tested on the migration of human skin fibroblasts in the 3D collagen gel assay, as previously used to demonstrate the motogenic activity of IGD synthetic peptides (S. L. Schor, I. Ellis, J. Banyard, and A. M. Schor, *Journal of Cell Science*, 1999, 112, 3879).

The results were plotted and are shown on the graph depicted in FIG. 3 in which compound (IV) is referred to as BDP 1. The data are expressed as fold-stimulation of migration relative to control fibroblasts in the absence of test compound. The range of base-line (control) migration is indicated by the horizontal dotted lines. Significantly, the IGD peptidomimetic (IV) stimulated target cell migration with a bell-shaped dose-response similar in potency and profile to that of IGDS under the same assay conditions. The control reverse peptide (SDGI) was completely devoid of bioactivity in this assay.

The invention claimed is:

1. A compound of formula (III):

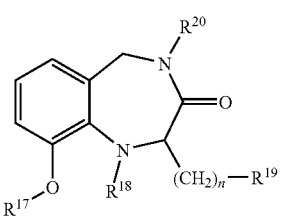

wherein, $R^{17}$ and $R^{20}$ are independently selected from H, a branched or unbranched substituted or unsubstituted linear or cyclic alkyl group, or a substituted or unsubstituted monocyclic or polycyclic aryl or heteroaryl group;

$R^{18}$ is H or a branched or unbranched substituted or unsubstituted linear or cyclic alkyl group;

$R^{19}$ is $CO_2R^{21}$;

$R^{21}$ is a branched or unbranched substituted or unsubstituted linear or cyclic alkyl group; and n is from 1 to 25, or a physiologically acceptable salt thereof.

2. The compound according to claim 1, of formula (IIIA):

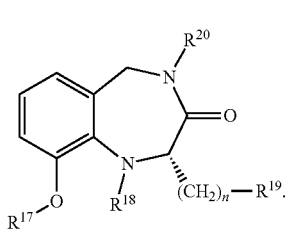

3. A compound of formula (IV):

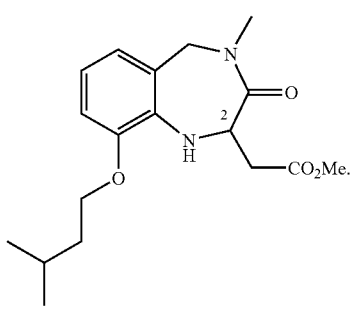

4. A pharmaceutical composition comprising the compound according to claim 1, and a pharmaceutically acceptable carrier therefor.

5. A pharmaceutical composition comprising the compound according to claim 1, and a pharmaceutically acceptable carrier therefor.

6. A pharmaceutical composition comprising the compound according to claim 2, and a pharmaceutically acceptable carrier therefor.

7. A pharmaceutical composition comprising the compound according to claim 3, and a pharmaceutically acceptable carrier therefor.

* * * * *

UNITED STATES PATENT AND TRADEMARK OFFICE
CERTIFICATE OF CORRECTION

PATENT NO. : 8,242,108 B2  
APPLICATION NO. : 12/064535  
DATED : August 14, 2012  
INVENTOR(S) : Schor et al.

Page 1 of 1

It is certified that error appears in the above-identified patent and that said Letters Patent is hereby corrected as shown below:

Column 2, Line 47: Please correct "or —$(CCR^{10}R^{11})_n$—;"
to read -- or —$(CR^{10}R^{11})_n$—; --

Column 4, Line 32: Please correct "or —$(CH_2)$—;"
to read -- or —$(CH_2)_n$—; --

Column 4, Line 47: Please correct "via —$(CH_2)$—, $R^4$"
to read -- via —$(CH_2)_n$—, $R^4$ --

Signed and Sealed this
Fifth Day of February, 2013

Teresa Stanek Rea
*Acting Director of the United States Patent and Trademark Office*